(12) United States Patent
Kurd et al.

(10) Patent No.: US 11,039,841 B2
(45) Date of Patent: Jun. 22, 2021

(54) SURGICAL RONGEUR WITH MODIFIED FOOTPLATE

(71) Applicant: A&K SPINAL INSTRUMENTS, INC., Wayne, PA (US)

(72) Inventors: Mark Kurd, Wayne, PA (US); David Greg Anderson, Villanova, PA (US); Shanu Kohli Kurd, Wayne, PA (US); Sam Sarcia, Lakeside, CA (US)

(73) Assignee: A&K Spinal Instruments, Inc., Wayne, PA (US)

( * ) Notice: Subject to any disclaimer, the term of this patent is extended or adjusted under 35 U.S.C. 154(b) by 101 days.

(21) Appl. No.: 16/178,746

(22) Filed: Nov. 2, 2018

(65) Prior Publication Data

US 2019/0150952 A1 May 23, 2019

Related U.S. Application Data

(60) Provisional application No. 62/588,976, filed on Nov. 21, 2017.

(51) Int. Cl.
*A61B 17/16* (2006.01)

(52) U.S. Cl.
CPC ................ *A61B 17/1611* (2013.01)

(58) Field of Classification Search
CPC ............ A61B 17/1604; A61B 17/1606; A61B 17/1608; A61B 17/1611
USPC .......................................................... 606/83
See application file for complete search history.

(56) References Cited

U.S. PATENT DOCUMENTS

| 5,451,227 A | 9/1995 | Michaelson |
| 5,653,713 A | 8/1997 | Michelson |
| 10,709,459 B2 * | 7/2020 | Eckermann ........ A61B 17/1604 |
| 2007/0093843 A1 | 4/2007 | Schneiter |
| 2014/0100593 A1 | 4/2014 | Sand |

(Continued)

FOREIGN PATENT DOCUMENTS

| WO | 2016/076585 | 5/2016 | |
| WO | WO-2016076585 A1 * | 5/2016 | ............ A61B 17/32 |
| WO | 2016/154030 | 9/2016 | |

OTHER PUBLICATIONS

Mitha, Alim P.; "A Modified Footplate for the Kerrison Rongeur", Department of Mechanical Engineering, Massachusetts Institute of Technology, Journal of Medical Devices, Mar. 2010, vol. 4/ 014502-1.

*Primary Examiner* — Si Ming Ku

(74) *Attorney, Agent, or Firm* — Rankin, Hill & Clark LLP

(57) ABSTRACT

A rongeur includes a lower member, a footplate, an upper member and an extension. The lower member is elongate along a first longitudinal axis. The footplate extends upwardly from a distal end portion of the lower member. The footplate includes a first cutting element that defines an apex spaced farthest upwardly from the first longitudinal axis. The upper member includes a second cutting element and is movable relative to the lower member. The extension is provided on the footplate and fixed to the footplate. The extension extends away from the first cutting element a maximum distance D1 measured upwardly from the apex and a maximum distance D2 measured laterally from the first cutting element and perpendicular to D1, where D1≠D2, and when D1>0 the extension is laterally confined between opposite lateral sides of the footplate above the apex of the first cutting element in an upward direction.

19 Claims, 10 Drawing Sheets

(56) References Cited

U.S. PATENT DOCUMENTS

2016/0106440 A1 4/2016 Harper
2016/0302801 A1 10/2016 Redmond et al.

* cited by examiner

SURGICAL RONGEUR WITH MODIFIED FOOTPLATE

BACKGROUND

Kerrison rongeurs, are surgical instruments used to remove portions of bone, cartilage or other tissue. Kerrison rongeurs may be used as a bone punch during neurosurgical and spinal procedures. When Kerrison rongeurs are used to remove bone, cartilage or other tissue during a neurosurgical or spinal procedure, there is a risk that a portion of the dura mater, which surrounds the spine, may creep between cutting blades of the Kerrison rongeur. Dural creep may result in a dural tear, which is undesirable.

FIG. 1 depicts a known Kerrison rongeur 10, hereinafter referred to as a surgical rongeur, including a lower member 12 that is elongate along a first longitudinal axis L1 between a proximal end portion 14 and a distal end portion 16. A footplate 18 is disposed at the distal end portion 16 of the lower member 12. The footplate 18 extends upwardly from the distal end portion 16 and the first longitudinal axis L1. The footplate 18 includes a first cutting element 20 that faces towards the proximal end portion 14 of the lower member 12 and a distal surface 22 that is disposed opposite the first cutting element 20 facing away from the proximal end portion 14. A handle 24 extends downwardly from the lower member 12 and includes a proximal extension 26. The handle 24 may be integral with lower member 12.

The surgical rongeur 10 also includes an upper member 28 elongate along a second longitudinal axis L2 between a proximal end portion 30 and a distal end portion 32. The second longitudinal axis L2 is substantially parallel to the first longitudinal axis L1. The upper member 28 includes a second cutting element 34 that is configured to cooperate with first cutting element 20 of the lower member 12 to remove bone, cartilage or other tissue. The upper member 28 is movable relative to the lower member 12 along the second longitudinal axis L2.

A lever 36 is operatively connected with the lower member 12 and the upper member 28. A first (upper) end portion 38 of the lever 36 is received in a recess 40 provided in the upper member 28 and a pivot pin 42 attaches the lever 36 to the lower member 12 and/or handle 24. A damper 44, such as a spring, is disposed between the handle 24 and the lever 36. In use, the lever 36 is actuated (squeezed) to move the upper member 28 with respect to the lower member 12. As the lever 36 pivots toward handle 24, the upper member 28 slides along the second longitudinal axis L2 towards the footplate 18 such that the first cutting element 20 and second cutting element 34 together engage a portion of a bone, cartilage or other tissue so as to remove the portion of the bone, cartilage or other tissue. During this procedure, there is a risk that dura mater will creep around the distal surface 22 of the footplate 18, and in between the first cutting element 20 and second cutting element 34, which may result in a dural tear.

FIG. 2 depicts another known Kerrison rongeur 50 that is similar in all respects to the surgical rongeur 10 shown in FIG. 1, with the exception that the surgical rongeur 50 includes a lower member 52 and an upper member 54 having a bayonet configuration. FIGS. 1 and 2 show only two different types of known surgical rongeurs, and many more are known to those skilled in the art. Known surgical rongeurs can also take alternative configurations, such as where the cutting elements are disposed at a right angle to the respective longitudinal axes.

There have been attempts to modify a surgical rongeur to mitigate against dura mater creeping between the cutting elements when bone, cartilage or other tissue are being removed. WO 2016/154030 A1 discloses providing a retractable flange made up of a cable disposed in a recess provided in the lower member of the surgical rongeur. The cable is actuated at a proximal end of the surgical rongeur to enlarge and contract a loop made by the cable in lateral and transverse directions relative to longitudinal axes. WO 2016/154030 A1 also discloses paddles mounted to the cable that are retractable to move dura mater away from the cutting elements. Both versions of the retractable flange require an additional trigger on the surgical rongeur.

WO 2016/076585 A1 discloses a surgical rongeur in which a pinch preventing protrusion is formed to protrude from the footplate. WO 2016/076585 A1 discloses the pinch preventing protrusion offset from the cutting element on the footplate in a distal direction parallel to the first longitudinal axis an offset distance that is at least as great as one-half the thickness of the footplate measured in the same direction, i.e., parallel to the first longitudinal axis. WO 2016/076585 A1 discloses a U-shaped pinch preventing protrusion when viewed normal to the first longitudinal direction having a uniform width (0.5 mm) around the periphery of the footplate, i.e., in both left and right lateral and upward dimensions. A pinch preventing protrusion having this configuration may not be suitable when the surgeon is working in very tight spaces.

There have been other modified surgical rongeurs where a protrusion having a uniform width, similar to WO 2016/076585 A1, have been provided on the footplate. Also, a paddle-shaped extension has been attached to the distal surface of the footplate. The paddle-shaped extension is relatively large and extends upwardly away from an apex of the cutting element of the footplate. No part of the paddle extends off of a lateral side of the footplate, however, the paddle, which is positioned entirely above an upper surface of the footplate does extend outwardly beyond the lateral sides of the footplate. These devices suffer from the same disadvantages of the surgical rongeur disclosed in WO 2016/076585 A1, i.e., the protrusions and paddles are not suitable for working in tight spaces.

SUMMARY

In view of the foregoing, a rongeur includes a lower member, a footplate, an upper member and an extension. The lower member is elongate along a first longitudinal axis. The footplate extends upwardly from a distal end portion of the lower member. The footplate includes a first cutting element facing toward a proximal end portion of the lower member and a distal surface facing away from the proximal end portion of the lower member. The first cutting element defines an apex spaced farthest upwardly from the first longitudinal axis. The upper member is elongate along a second longitudinal axis. The upper member includes a second cutting element configured to cooperate with the first cutting element to remove bone, cartilage or other tissue. The upper member is movable relative to the lower member along the second longitudinal axis. The extension is provided on the footplate and fixed to the footplate so as not to be movable with respect to the footplate during a surgical procedure. The extension extends away from the first cutting element a maximum distance D1 measured upwardly from the apex of the first cutting element and a maximum distance D2 measured laterally from the first cutting element and perpendicular to D1, where D1≠D2, and when D1>0 the extension is laterally confined between opposite lateral sides of the footplate above the apex of the first cutting element in an upward direction.

Also in view of the foregoing, an extension for attaching to a Kerrison rongeur includes a footplate extension member and a retainer extending from the foot plate extension member. The foot plate extension member is configured to extend outwardly from a peripheral edge of a foot plate of an associated Kerrison rongeur to which the foot plate extension member removably attaches. The retainer is configured to retain the foot plate extension member fixed in place with respect to the foot plate of the associated Kerrison rongeur while a first cutting element of the associated Kerrison rongeur is moved with respect to a second cutting element of the associated Kerrison rongeur.

DETAILED DESCRIPTION

Figures 1, 2:
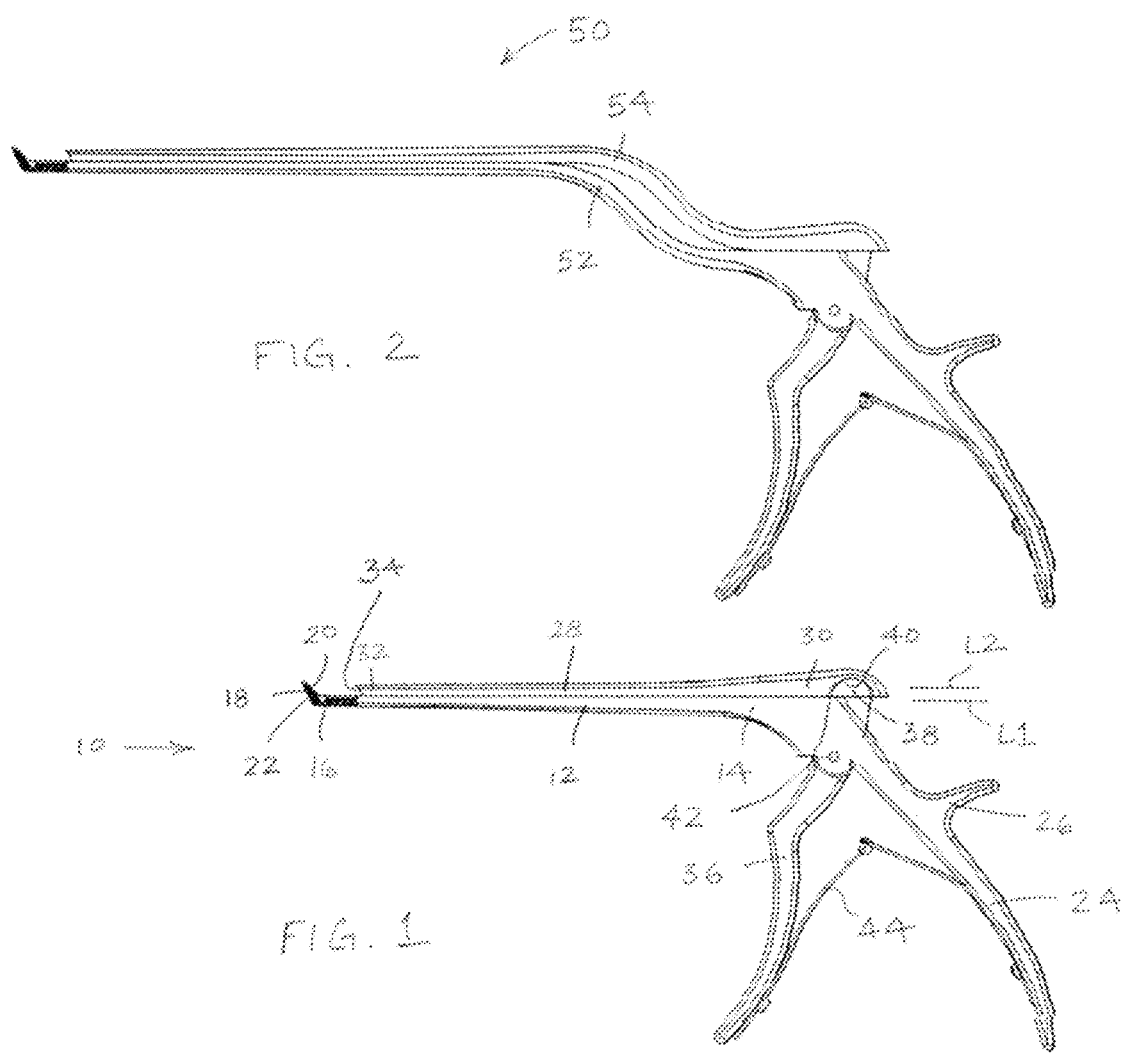
FIG. 1 is a side view of a known surgical rongeur.
FIG. 2 is a side view of another known surgical rongeur.
Figure 3:
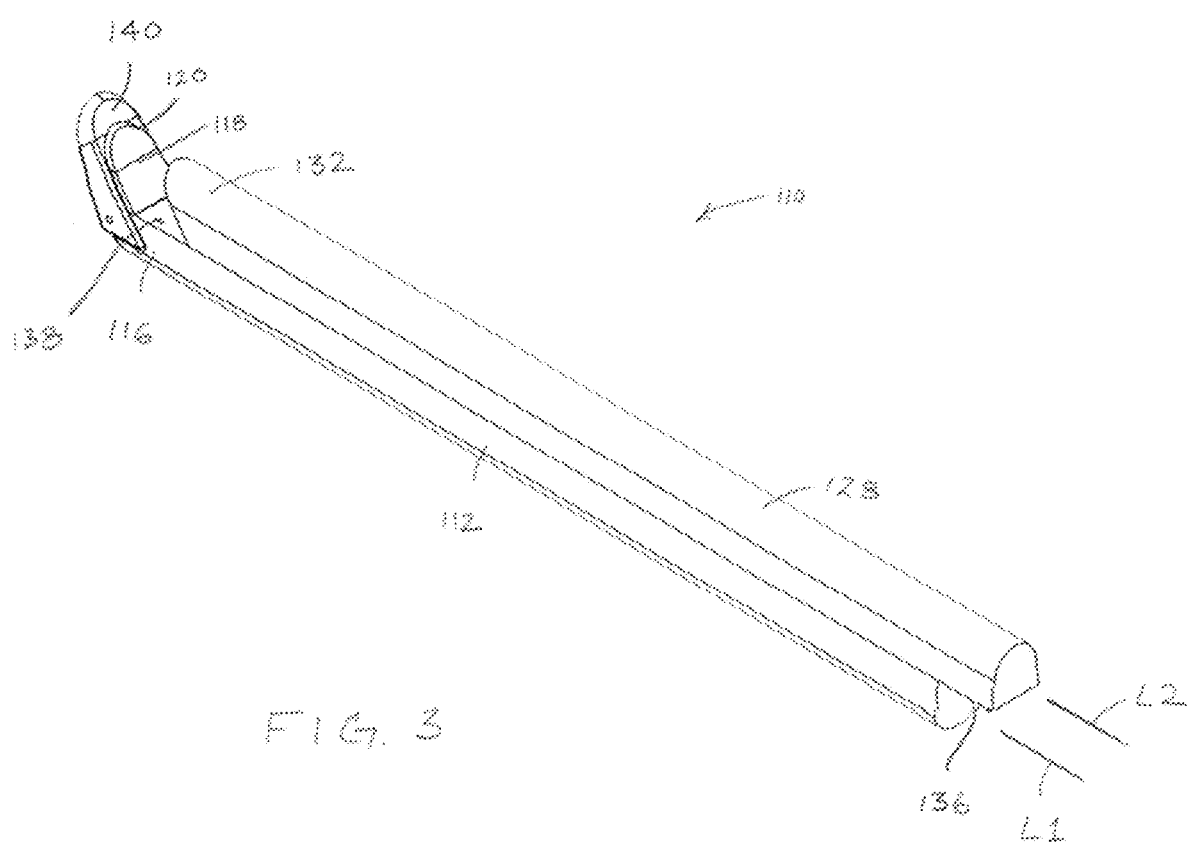
FIG. 3 is a perspective view of a distal portion of a surgical rongeur having a footplate extension.
Figure 4:
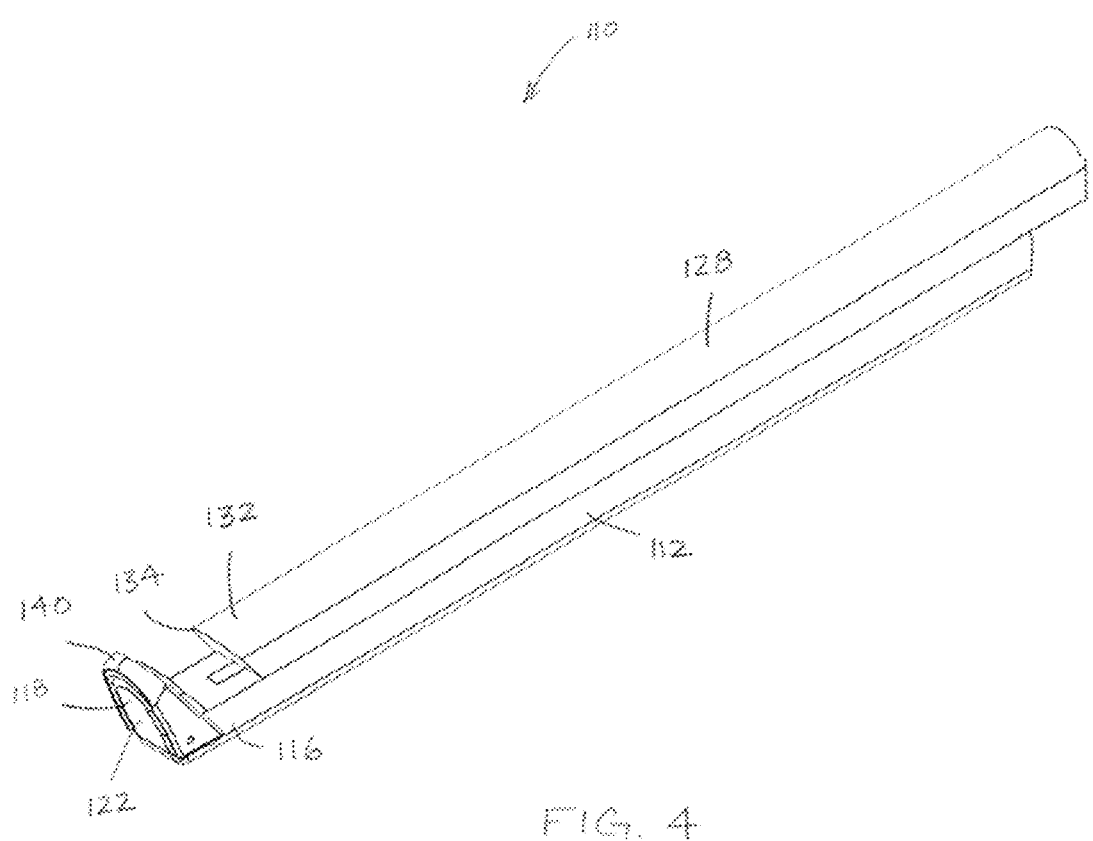
FIG. 4 is a perspective view of the distal portion of the surgical rongeur in FIG. 3 viewed from 180 degrees from the view shown in FIG. 3.

FIGS. 3 and 4 depict a distal section of a surgical rongeur 110 useful to mitigate the likelihood of dural tears. The surgical rongeur 110 includes a lower member 112 that is elongate along a first longitudinal axis L1 between a proximal end portion (not visible in FIGS. 3 and 4) and a distal end portion 116. A footplate 118 is disposed at the distal end portion 116 of the lower member 112. The footplate 118 extends upwardly from the distal end portion 116 and the first longitudinal axis L1. The footplate 118 includes a first cutting element 120 that faces towards the proximal end portion of the lower member 112 and a distal surface 122 that is disposed opposite the first cutting element 120 facing away from the proximal end portion. The surgical rongeur 110 also includes an upper member 128 elongate along a second longitudinal axis L2 between a proximal end portion (not visible in FIGS. 3 and 4) and a distal end portion 132. The second longitudinal axis L2 is substantially parallel to the first longitudinal axis L1. The upper member 128 includes a second cutting element 134 that is configured to cooperate with first cutting element 120 of the lower member 112 to remove bone, cartilage or other tissue. The upper member 128 is movable relative to the lower member 112 along the second longitudinal axis L2 in the same manner that the upper member 28 is movable relative to the lower member 12. A lower surface 136, which is planar, of the upper member 28 rides along an upper surface 138, which is also planar, of the lower member 112. The remaining proximal section of the surgical rongeur is not shown in FIGS. 3 and 4 and can be similar to the proximal section of the surgical rongeurs 10 and 50 depicted in FIGS. 1 and 2.

The surgical rongeur 110 differs from the surgical rongeurs 10 and 50 depicted in FIGS. 1 and 2 in that the surgical rongeur 110 includes an extension 140 provided on the footplate 118 and fixed to the footplate 118 so as not to be movable with respect to the footplate 118 during a surgical procedure. This obviates the need for a separate trigger on the surgical rongeur 110 to deploy the extension 140.

Figure 5:
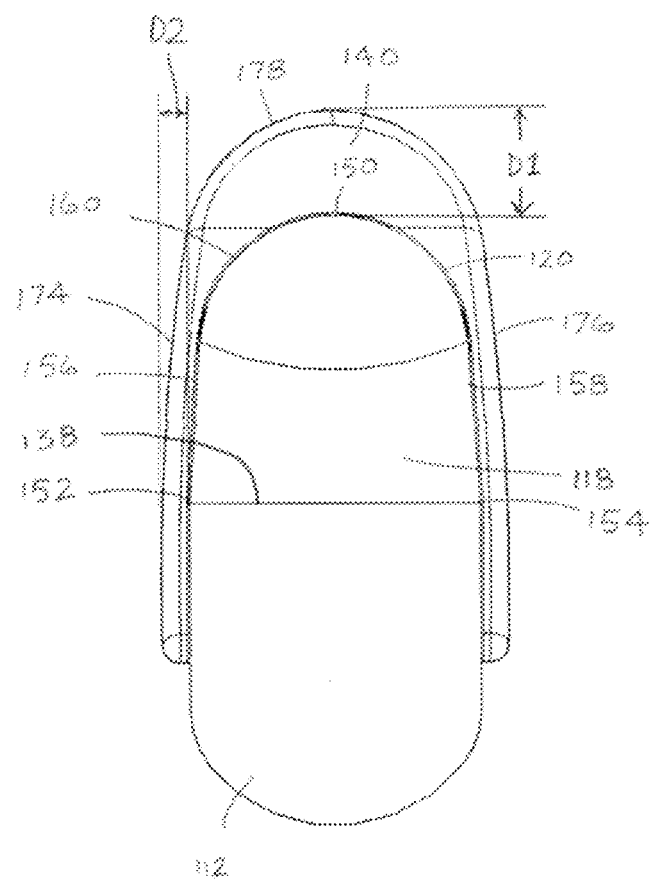
FIG. 5 is a cross-sectional view taken normal to a longitudinal axis of a lower member of the surgical rongeur in FIG. 3 looking toward the distal end of the surgical rongeur.

With reference to FIG. 5, the first cutting element 120 defines an apex 150 where the first cutting element 120 is spaced farthest upwardly from the upper surface 138 of the lower member 112 and the first longitudinal axis L1. As seen in FIG. 5, the first cutting element 120 is generally upside down U-shaped in configuration extending generally upwardly from a lower left base 152 to the apex 150 and then back downwardly toward a lower right base 154. With continued reference to FIG. 5, the footplate 118 also includes a left lateral side 156 and a right lateral side 158. A curved upper surface 160 connects the left lateral side 156 to the right lateral side 158.

With reference to FIG. 5, the extension 140 extends away from the first cutting element 120, a maximum distance D1 measured upwardly from the apex 150 of the first cutting element 120, and a maximum distance D2 measured laterally from the first cutting element 120 in a direction perpendicular to D1. As is apparent in FIG. 5, D1 does not equal D2. In FIG. 5, D1 is greater than D2. In the embodiment illustrated in FIG. 5, D1 is greater than D2×2. Moreover, D1 can be greater than D2×7. Also, D1 can be less than D2×10 so that the anterior extension does not get too great. As illustrated in FIG. 5, D2 could be less than 0.3 mm and D1 can be up to 2 mm. Also, above the apex 150 of the first cutting element 120 in the upward direction, the extension 140 is laterally confined between the opposite lateral sides 156, 158 of the footplate 118. As such, a lateral dimension of the extension 140, which is measured parallel to D2, above the apex 150 only decreases moving upwardly away from the apex 150.

Figure 6:
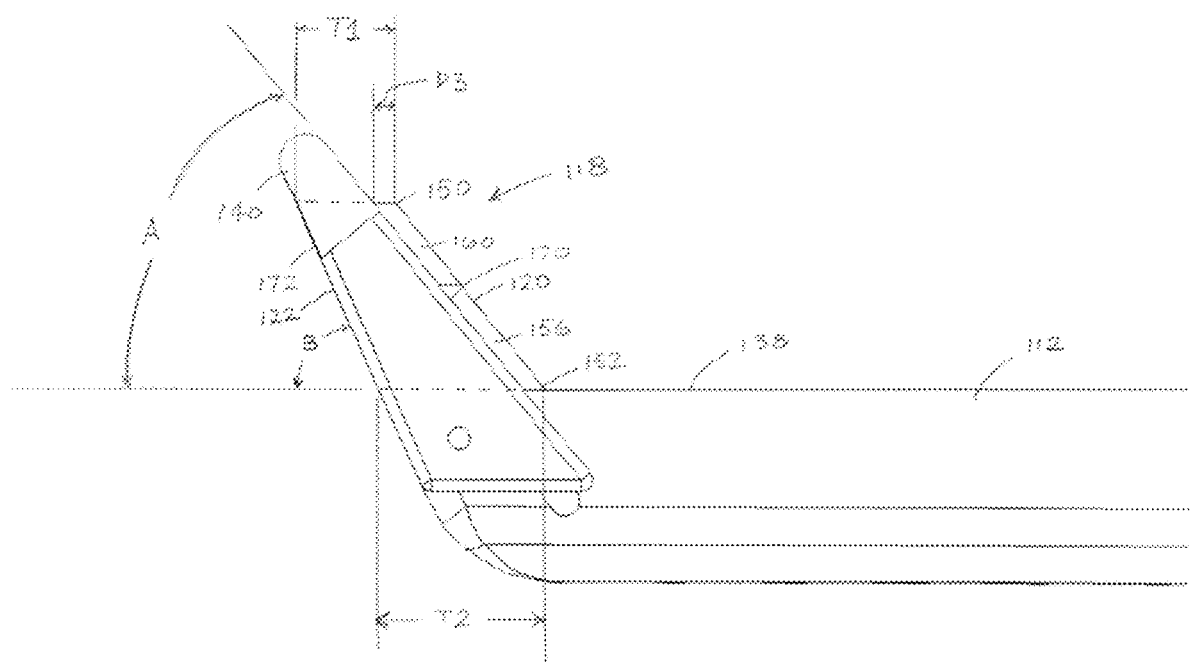
FIG. 6 is a side view of the distal portion of the surgical rongeur in FIG. 3.

With reference to FIG. 6, the extension 140 includes a proximal face 170 facing towards the proximal end of the lower member 112 and a distal face 172 facing away from the proximal end of the lower member 112. With reference back to FIG. 5, the extension 140 includes a left lateral outer side surface 174 and a right lateral outer side surface 176. A curved upper surface 178 interconnects the left lateral outer side surface 174 with the right lateral outer side surface 176. With reference back to FIG. 6, the proximal face 170 of the extension 140 is offset at an internal angle A from the first longitudinal axis L1. The distal face 172 of the footplate 118 is offset at an internal angle B from the first longitudinal axis L1. The proximal face 170 of the extension 140 is not parallel to the distal face 172 in the embodiment illustrated in FIG. 6. Also, the internal angle A is less than 90° and greater than the internal angle B in the embodiment illustrated in FIG. 6.

With continued reference to the embodiment depicted in FIG. 6, the proximal face 170 of the extension 140 is offset from the first cutting element 120 in a distal direction measured parallel to the first longitudinal axis L1. In the illustrated embodiment, the proximal face 170 of the extension 140 is offset a distance D3 from the first cutting element 120. The proximal face 170 of the extension 140 is positioned nearer to the first cutting element 120 as compared to the distal surface 122 of the footplate 118. Also, D2 (FIG. 5) in the illustrated embodiment is less than D3. With continued reference to FIG. 6, the distal surface 122 of the footplate 118 is coplanar with the distal face 172 of the extension 140. In an alternative embodiment, the distal face 172 of the extension 140 can be offset from the distal surface 122 of the footplate 118 in a proximal direction (toward the proximal end of the lower member 112) measured parallel to the first longitudinal axis L1.

With continued reference to the embodiment depicted in FIG. 6, the footplate 118 can have a first thickness T1 measured parallel to the first longitudinal axis L1 between the apex 150 of the first cutting element 120 and the distal surface 122. The footplate 118 can also have a second thickness T2 measured parallel to the first longitudinal axis L1 between the base 152, 154 of the first cutting element 120 and the distal surface 122. As depicted T1 is less than T2.

Figure 7:
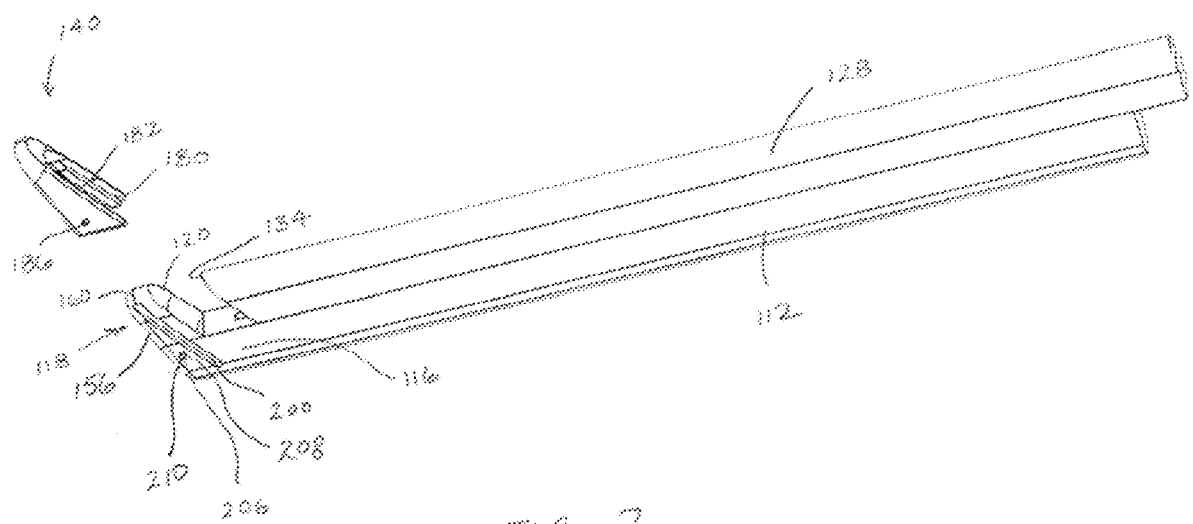
FIG. 7 is a perspective view of the distal portion of the surgical rongeur of FIG. 3 with the footplate extension removed from the footplate.

The extension 140 can be configured to be connected with the footplate 118 so as to be fixed to and not movable with respect to the footplate 118 once connected. The extension 140 as shown in FIG. 7 can be generally upside down U-shaped having an internal surface 180 that is complementary in shape such that the internal surface 180 conforms to or matches the left lateral side 156, the curved upper surface 160, and the right lateral side 158 of the footplate 118. As seen in FIG. 5, very little or no gap is provided between the internal surface 180 and the peripheral edge of the footplate 118, which is made up of the left lateral side 156, the curved upper surface 160, and the right lateral side 158, when the extension 140 is connected with the footplate 118 so as to be fixed to and not movable with respect to the footplate 118.

The extension 140 includes projections such as a left projection (not visible) and a right projection 182, which is a mirror image of the left projection. Each projection 182 extends inwardly from the internal surface 180. The projections 182 are elongate in a direction transverse to the first longitudinal axis L1 and are generally vertically oriented as shown in FIG. 7. The extension 140 also includes openings such as a left opening 186 and a right opening (not visible), which is aligned with the left opening 186 in a direction perpendicular to the first longitudinal axis L1. Alternatively, recesses in a similar location to the left opening 186 and the right opening can be provided in the extension 140.

The footplate 118 includes a left slot 200 and a right slot (not visible in FIG. 7 but similarly oriented to the left slot 200). The left slot 200 and the right slot (not visible) are configured to receive the left projection (not visible) and the right projection 182, respectively. With the projections 182 received in the slots 200, the extension 140 is fixed to the footplate 118 such that movement of the extension 140 with respect to the footplate 118 in a direction parallel to the first longitudinal axis L1 is precluded. A left protuberance 206 extends from the left lateral side 156 of the footplate 118. The left protuberance 206 is received inside the left opening 186 in the extension 140. A right protuberance (not visible) similar to and aligned in a direction perpendicular to the first longitudinal axis L1 with the left protuberance 206 extends from the right lateral side 158 of the footplate 118 so as to be received in a similar opening on the right side of the extension 140.

The extension 140 is configured to be connected with the footplate 118 so as to be fixed to and not movable with respect to the footplate 118. The location of the projections 182 and the slots 200 can be reversed such that slots can be provided on the extension 140 and projections can be provided on the footplate 118. As such, one or more slots (similar to slots 200) can be provided in one of the extension 140 and the footplate 118, and one or more projections (similar to the projection 182) can be provided on one of the extension 140 and the footplate 118. The extension 140 is movable between an engaged position in which the one or more projections 182 are in the one or more slots 200 and a disengaged position in which the one or more projections are not in the one or more slots 200. The extension 140 is precluded from movement with respect to the lower member 112 in the direction parallel to the first longitudinal axis L1 when the extension 140 is in the engaged position.

The location of the openings 186 and protuberances 206 can be reversed in that protuberances can be provided on the internal surface 180 of the extension 140 and holes or recesses can be provided on the footplate 118 for receiving the protuberances. As such, one or more openings 186 or recesses can be provided in one of the extension 140 and the footplate 118, and one or more protuberances 206 extend from one of the extension 140 and the footplate 118. The one or more protuberances 206 are received in the one or more openings 186 or recesses when the extension is in a fully engaged position. When the extension 140 is in the fully engaged position, the extension 140 is precluded from movement with respect to the lower member 112 in three mutually perpendicular axes, e.g., in X, Y and Z.

In the embodiment depicted in FIG. 7, the extension 140 is provided with the one or more openings 186 and the footplate includes a pin passage 208 that receives a pin 210 to provide the one or more protuberances 206 extending from the footplate 118. The pin 210 can be received in the openings 186 on the extension 140 and though the pin passage 208 to connect the extension 140 with the footplate 118.

The extension 140 depicted in FIGS. 3-7 is shown as connecting to the footplate 118 so as to be detachable from the footplate and therefore may be referred to as a clip that selectively clips onto the surgical rongeur 110. The extension 140 can also be fixed to or integrally formed with and not movable with respect to the footplate 118. For example, during the manufacture of the surgical rongeur 110, the footplate 118 can be formed to include the extension 140 extending away from the first cutting element 120 where the extension is shaped in the manner similar to that shown in FIGS. 3-6. Alternatively, the footplate 118 can be provided shaped similar to that shown in FIG. 7, but without the slots 200 and protuberances 206, e.g., similar to a known Kerrison rongeur. The same metal from which the footplate 118 has been manufactured, can be added, e.g., welded, to the appropriate locations along the lateral sides 156, 158 and the curved upper surface 160 to permanently attach and provide the extension 140 on the footplate 118.

Figure 8:
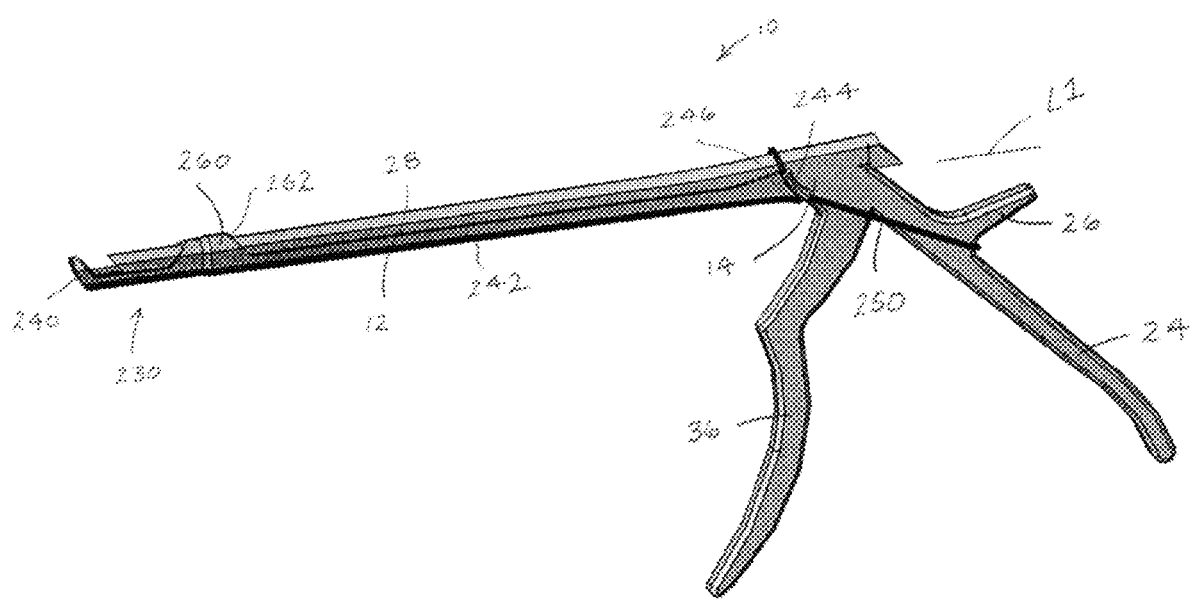
FIG. 8 is a perspective view of a surgical rongeur having an alternative footplate extension attached thereto.

FIG. 7 shows one embodiment by which the extension 140, in the form of a clip, can be attached to the footplate 118. FIG. 8 depicts another example of an extension 230 for attaching to the surgical rongeur 10 including a footplate extension member 240 and retainer 242 extending from the footplate extension member 240. The footplate extension member 240 extends outwardly from a peripheral edge of the footplate 118 and can be similarly shaped to the extension 140 shown in FIGS. 3-6. The retainer 242 extends from the footplate extension member 240 and retains the footplate extension member 240 fixed in place, i.e., in three mutually perpendicular axes, with respect to the footplate 18 of the surgical rongeur 10 while the second cutting element 134 is moved with respect to the first cutting element 120.

The retainer 242 is elongate in a direction parallel with the first longitudinal axis L1. The retainer 242 can be generally U-shaped in a cross section normal to the first longitudinal axis L1. The retainer 242 can conform in shape to the lower member 12 in the cross section normal to the first longitudinal axis L1 such that the retainer 242 snuggly receives the lower member 12. Instead of being U-shaped in cross section, the retainer 242 could include left and right arms that extend along respective left and right lateral sides of the lower member 12 that are not interconnected underneath the lower member 12 but instead simply extend in a proximal direction from the footplate extension member 240. The retainer 242 includes tension band connectors 244 (only one is visible in FIG. 8) at a proximal end section 246 of the retainer 242. The tension band connectors 244 as depicted are curled over sections configured to receive a tension band 250 that loops over the proximal extension 26 on the handle 24 of the surgical rongeur 10. The tension band 250 pulls the extension 230 in a proximal direction along the first longitudinal axis L1 to retain the extension 230 on the surgical rongeur 10.

The extension 230 also includes a hood 260 that interconnects opposite lateral sides of the retainer 242. The hood 260 and the retainer 242 define a passage 262 that receives the distal end sections of the lower member 12 and the upper member 28 of the surgical rongeur 10 and allows the upper member 28 to move with respect to the lower member 12. The passage 262 closely conforms in cross section to the cross sectional configuration of the upper member 28 and lower member 12 received through the passage 262. The wall thickness of the retainer 242 and the hood 260 is preferably minimized (e.g., less than about 0.3 mm), which can allow the surgical rongeur 10 with the extension 230 attached thereto to be used nearly in every instance in which the surgical rongeur 10 without the extension 230 attached thereto could be used.

Figure 9:
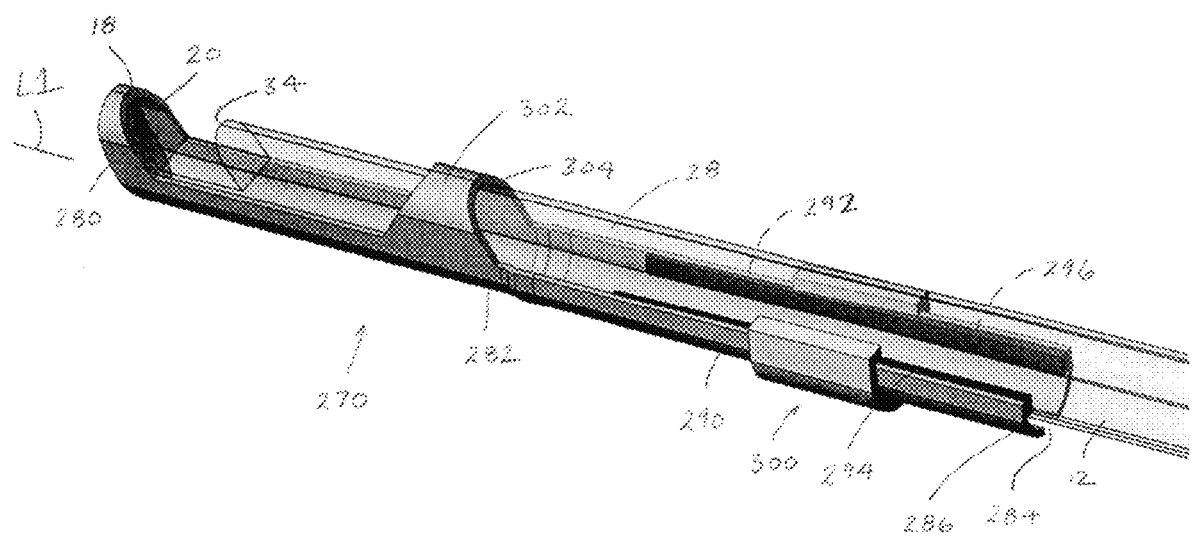
FIG. 9 is a perspective view of a distal portion of a surgical rongeur having another alternative footplate extension attached thereto.

FIG. 9 depicts another embodiment of an extension 270 for attaching to a surgical rongeur (similar to the surgical rongeur 10 depicted in FIG. 8). The extension 270 depicted in FIG. 9 includes a footplate extension member 280 and retainer 282 extending from the footplate extension member 280. The footplate extension member 280 extends outwardly from a peripheral edge of the footplate 18 to which the footplate extension member 280 removably attaches. The retainer 282 retains the footplate extension member 280 fixed in place, i.e., in three mutually perpendicular axes, with respect to the footplate 18 of the surgical rongeur 10 while the second cutting element 34 is moved with respect to the first cutting element 20. The footplate extension member 280 can be similarly shaped to the extension 140 depicted in FIGS. 3-6.

The retainer 282 can be U-shaped in cross section taking normal to the first longitudinal axis L1. The retainer 282 can conform to the outer peripheral surface of the lower member 12 and have a thin wall thickness (e.g., 0.3 mm or less). An elongate slot 284 extends in a distal direction parallel to the first longitudinal axis L1 from a proximal end 286 of the retainer 242. Accordingly, a left arm 290 and a right arm 292 are separated by the slot 284. A friction pad, e.g., a left friction pad 294 and a right friction pad 296, are provided on inner surfaces of the left arm 290 and the right arm 292, respectively. The friction pads 294, 296, which can be made from a rubber-like material, frictionally engage an outer surface of the lower member 12 to retain the extension 270 to the surgical rongeur 10.

A clamp 300, which can be U-shaped in a cross section taken normal to the first longitudinal axis L1, can slide over the retainer 282, and more particularly the left arm 290 and the right arm 292 to urge the friction pads 294, 296 toward the lateral surfaces of the lower member 12. The extension 270 also includes a hood 302 that interconnects opposite lateral sides of the retainer 242. The hood 302 and the retainer 282 define a passage 304 that is similar in cross sectional configuration (normal to the first longitudinal axis L1) to that of the lower member 12 and the upper member 28 so that the upper member 28 can move with respect to the lower member 12 within the passage 304. The wall thickness of the hood 302 is similar to that of the retainer 282 (e.g., less than 0.30 mm).

Figure 10:
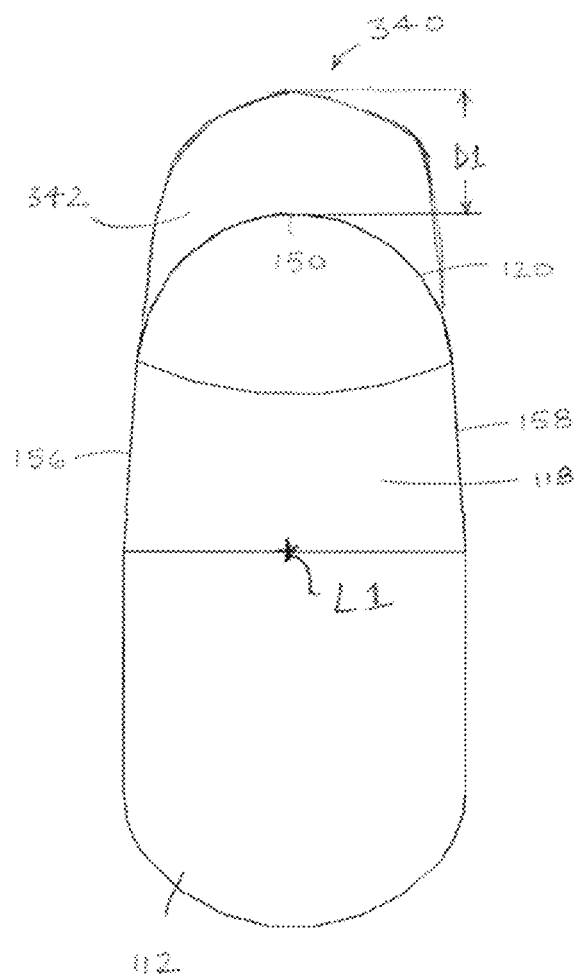
FIG. 10 is a cross-sectional view taken normal to a longitudinal axis of a lower member of a surgical rongeur similar to FIG. 3 looking toward the distal end of the surgical rongeur having a footplate extension with an alternative shape to that shown in FIG. 5.

FIG. 10 depicts an alternative extension 340 shaped differently than the extension 140 described above. In FIG. 10, the extension 340 extends away from the first cutting element 120, a maximum distance D1 measured upwardly from the apex 150 of the first cutting element 120; however, the extension 340 does not extend laterally from the first cutting element 120 in a direction perpendicular to D1. In the embodiment depicted in FIG. 5, D2 is a dimension greater than 0, however, for the embodiment depicted in FIG. 10 D2=0. Like the embodiment depicted in FIG. 5, for the embodiment depicted in FIG. 10 D1 does not equal D2, and D1 is greater than D2. For the embodiment depicted in FIG. 10, D1 can be up to 2 mm. Above the apex 150 of the first cutting element 120 in the upward direction, the extension 340 is laterally confined between the opposite lateral sides 156, 158 of the footplate 118. As such, a lateral dimension of the extension 140, which is measured parallel to D2 (perpendicular to D1), above the apex 150 only decreases moving upwardly away from the apex 150. The extension 340 includes a proximal face 342 that is offset from the first cutting element 120 in a distal direction measured parallel to the first longitudinal axis L1. Like the embodiment depicted in FIG. 5, the proximal face 342 of the extension 340 is positioned nearer to the first cutting element 120 as compared to the distal surface 122 (not visible in FIG. 10) of the footplate 118.

Figure 11:
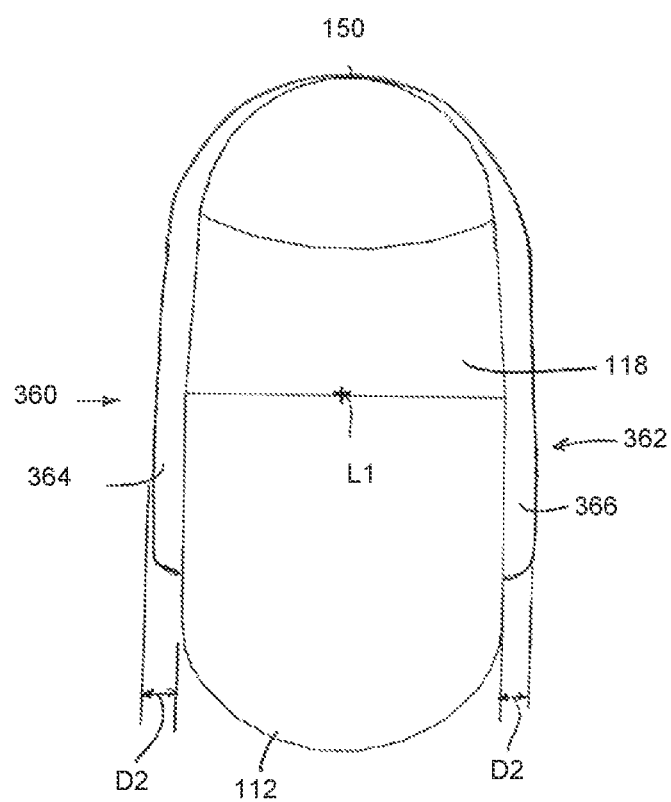
FIG. 11 is a cross-sectional view taken normal to a longitudinal axis of a lower member of a surgical rongeur similar to FIG. 3 looking toward the distal end of the surgical rongeur having a footplate extension with another alternative shape to that shown in FIG. 5.

FIG. 11 depicts another alternative extension, which can include a left lateral extension 360 and a right lateral extension 362. Alternatively, only one of the lateral extensions may be provided. In FIG. 11, each lateral extension 360, 362 extends away from the first cutting element 120, a maximum distance D2 measured perpendicular to the first longitudinal axis L1 and neither lateral extension 360, 362 extends upwardly from or above the apex 150 of the first cutting element 120. In the embodiment depicted in FIG. 5, D1 is a dimension greater than 0, however, for the embodiment depicted in FIG. 11 D1=0. Like the embodiment depicted in FIG. 5, for the embodiment depicted in FIG. 11 D1 does not equal D2, and D2 is greater than D1. For the embodiment depicted in FIG. 10, D2 can be up to 2 mm. Each extension 360, 362 includes a respective proximal face 364, 366 that is offset from the first cutting element 120 in a distal direction measured parallel to the first longitudinal axis L1. Like the embodiment depicted in FIG. 5, each proximal face 364, 366 is positioned nearer to the first cutting element 120 as compared to the distal surface 122 (not visible in FIG. 11) of the footplate 118.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A rongeur comprising:
   a lower member elongate along a first longitudinal axis;
   a footplate extending upwardly from a distal end portion of the lower member, the footplate including a first cutting element facing toward a proximal end portion of the lower member and a distal surface facing away from the proximal end portion of the lower member, the first cutting element defining an apex spaced farthest upwardly from the first longitudinal axis;
   an upper member elongate along a second longitudinal axis, the upper member including a second cutting element configured to cooperate with the first cutting element to remove bone, cartilage or other tissue, the upper member being movable relative to the lower member along the second longitudinal axis;
   an extension provided on the footplate and fixed to the footplate so as not to be movable with respect to the footplate during a surgical procedure, the extension extending away from the first cutting element having a maximum distance D1 measured upwardly from the apex of the first cutting element and a maximum distance D2 measured laterally from the first cutting element and perpendicular to D1, wherein the extension is configured to be connected with the footplate so as to be fixed to and not movable with respect to the footplate, wherein one or more slots are provided in one of the extension and the footplate, and one or more projections are provided on one of the extension and the footplate, the extension being movable between an engaged position in which the one or more projections are in the one or more slots and a disengaged position in which the one or more projections are not in the one or more slots;
   wherein D1≠D2, and
   when D1>0 the extension is laterally confined between opposite lateral sides of the footplate above the apex of the first cutting element in an upward direction.

2. The rongeur of claim 1, wherein D1>D2×2.
3. The rongeur of claim 1, wherein D1>D2×7.
4. The rongeur of claim 1, wherein D1<D2×10.
5. The rongeur of claim 1, wherein D2<0.3 mm.
6. The rongeur of claim 1, wherein the extension is precluded from movement with respect to the lower member in a direction parallel to the longitudinal axis when in the engaged position.
7. The rongeur of claim 6, wherein one or more holes or recesses are provided in one of the extension and the footplate, and one or more protuberances extend from one of the extension and the footplate, the one or more protuberances being received in the one or more holes or recesses when the extension is in a fully engaged position.
8. The rongeur of claim 7, wherein the extension is provided with the one or more holes and the footplate includes a pin passage that receives a pin to provide the one or more protuberances extending from the footplate.
9. The rongeur of claim 1, wherein the extension includes a proximal face facing towards the proximal end of the lower member and a distal face facing away from the proximal end of the lower member, wherein the proximal face of the extension is offset an angle A from the first longitudinal axis and the distal surface of the footplate is offset an angle B from the first longitudinal axis, wherein 90>A>B.
10. The rongeur of claim 9, wherein the proximal face of the extension is offset from the first cutting element in a distal direction.
11. The rongeur of claim 10, wherein the proximal face is positioned nearer to the first cutting element as compared to the distal surface of the footplate.
12. The rongeur of claim 1, wherein the extension includes a proximal face facing towards the proximal end of the lower member and a distal face facing away from the proximal end of the lower member, wherein the proximal face of the extension is offset from the first cutting element in a distal direction.
13. The rongeur of claim 12, wherein the proximal face is positioned nearer to the first cutting element as compared to the distal surface of the footplate.
14. The rongeur of claim 13, wherein the proximal face of the extension is offset an angle A from the first longitudinal axis and the distal surface of the footplate is offset an angle B from the first longitudinal axis, wherein 90>A>B.
15. The rongeur of claim 1, wherein the footplate has a first thickness T1 measured parallel to the first longitudinal axis between an apex of the first cutting element and the distal surface and a second thickness T2 measured parallel to the first longitudinal axis between a base of the first cutting element and the distal surface, wherein T1<T2.
16. The rongeur of claim 15, wherein the extension includes a proximal face facing towards the proximal end of the lower member and a distal face facing away from the proximal end of the lower member, wherein the distal face is coplanar with or offset from the distal surface in a proximal direction.
17. The rongeur of claim 1, wherein the extension includes a proximal face facing towards the proximal end of the lower member and a distal face facing away from the proximal end of the lower member, wherein the distal face is coplanar with or offset from the distal surface in a proximal direction.
18. The rongeur of claim 1, wherein the proximal face of the extension is offset from the first cutting element in a distal direction a distance D3, wherein D2<D3.
19. The rongeur of claim 1, wherein the proximal face of the extension is offset from the first cutting element in a distal direction a distance D3, wherein D2>D3.

* * * * *